(12) United States Patent
Yao et al.

(10) Patent No.: US 11,398,146 B2
(45) Date of Patent: Jul. 26, 2022

(54) EMERGENCY ASSISTANCE RESPONSE

(71) Applicant: Micron Technology, Inc., Boise, ID (US)

(72) Inventors: Chunhua Yao, Boise, ID (US); Priya Vemparala Guruswamy, Boise, ID (US); Xiao Li, Boise, ID (US); Cipriana Forgy, Meridian, ID (US); Anshika Sharma, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 17/147,508

(22) Filed: Jan. 13, 2021

(65) Prior Publication Data
US 2022/0198902 A1    Jun. 23, 2022

Related U.S. Application Data

(60) Provisional application No. 63/128,931, filed on Dec. 22, 2020.

(51) Int. Cl.
| | |
|---|---|
| *G08B 23/00* | (2006.01) |
| *G08B 21/04* | (2006.01) |
| *G08B 21/18* | (2006.01) |
| *G06F 9/54* | (2006.01) |

(52) U.S. Cl.
CPC .......... *G08B 21/043* (2013.01); *G06F 9/542* (2013.01); *G08B 21/182* (2013.01); *G08B 21/0446* (2013.01); *G08B 21/0453* (2013.01)

(58) Field of Classification Search
CPC ............... G08B 21/043; G08B 21/182; G08B 21/0446; G08B 21/0453; G06F 9/542

USPC ....................................... 340/573.1
See application file for complete search history.

(56) References Cited

U.S. PATENT DOCUMENTS

| | | | |
|---|---|---|---|
| 10,869,181 B2 | 12/2020 | Gideon, III | |
| 10,872,518 B2 | 12/2020 | Mien | |
| 2006/0282021 A1* | 12/2006 | DeVaul | A61B 5/0205 600/595 |
| 2010/0174424 A1* | 7/2010 | Cornell | G05B 23/0272 701/14 |
| 2012/0218123 A1* | 8/2012 | Ji | A61B 5/0022 340/870.07 |

(Continued)

*Primary Examiner* — Zhen Y Wu
(74) *Attorney, Agent, or Firm* — Brooks, Cameron & Huebsch, PLLC

(57) ABSTRACT

Methods, systems, and non-transitory machine-readable media associated with an emergency assistance response are described. A system for an emergency assistance response can include a non-transitory machine-readable medium comprising a processing resource in communication with a memory resource having instructions executable to receive signaling associated with monitored health data. The instructions can be executable to track the received signaling, identify, output data representative of abnormal health data based on the tracked received signaling, and transmit the output data to a wearable device. The wearable device can receive the output data representative of the abnormal health data, provide a prompt via a user interface to a wearer of the wearable device associated with the abnormal health data, determine a response to the abnormal health data based on a reply or non-reply from the wearer via the user interface, and transmit the response to the processing resource.

17 Claims, 7 Drawing Sheets

(56) References Cited

U.S. PATENT DOCUMENTS

| | | | |
|---|---|---|---|
| 2013/0070044 A1* | 3/2013 | Naidoo | G16Z 99/00 |
| | | | 348/14.02 |
| 2014/0152453 A1* | 6/2014 | Dahl | H04W 76/50 |
| | | | 340/686.6 |
| 2015/0269827 A1* | 9/2015 | Hopkins | G08B 21/0227 |
| | | | 340/539.12 |
| 2016/0012702 A1* | 1/2016 | Hart | G08B 21/18 |
| | | | 340/584 |
| 2017/0086569 A1* | 3/2017 | Grote | F21V 33/0004 |
| 2017/0358200 A1* | 12/2017 | Newman | A61B 5/746 |
| 2018/0012471 A1* | 1/2018 | Bauer | H04W 4/029 |
| 2019/0281433 A1* | 9/2019 | Newman | G08B 25/001 |
| 2020/0329358 A1* | 10/2020 | Hamre | H04M 3/5116 |
| 2020/0342735 A1 | 10/2020 | Tan et al. | |
| 2020/0342736 A1 | 10/2020 | Tan et al. | |
| 2020/0342737 A1 | 10/2020 | Pham et al. | |
| 2020/0373005 A1 | 11/2020 | Halsne et al. | |
| 2021/0153817 A1* | 5/2021 | Beyer | G16H 40/67 |

* cited by examiner

EMERGENCY ASSISTANCE RESPONSE

PRIORITY INFORMATION

This application is a Non-Provisional Application of U.S. Provisional Application No. 63/128,931, filed Dec. 22, 2020, the contents of which are herein incorporated by reference.

TECHNICAL FIELD

The present disclosure relates generally to apparatuses, non-transitory machine-readable media, and methods associated with emergency assistance response.

BACKGROUND

Memory resources are typically provided as internal, semiconductor, integrated circuits in computers or other electronic systems. There are many different types of memory, including volatile and non-volatile memory. Volatile memory can require power to maintain its data (e.g., host data, error data, etc.). Volatile memory can include random access memory (RAM), dynamic random-access memory (DRAM), static random-access memory (SRAM), synchronous dynamic random-access memory (SDRAM), and thyristor random access memory (TRAM), among other types. Non-volatile memory can provide persistent data by retaining stored data when not powered. Non-volatile memory can include NAND flash memory, NOR flash memory, and resistance variable memory, such as phase change random access memory (PCRAM) and resistive random-access memory (RRAM), ferroelectric random-access memory (FeRAM), and magnetoresistive random access memory (MRAM), such as spin torque transfer random access memory (STT RAM), among other types.

Electronic systems often include a number of processing resources (e.g., one or more processing resources), which may retrieve instructions from a suitable location and execute the instructions and/or store results of the executed instructions to a suitable location (e.g., the memory resources). A processing resource can include a number of functional units such as arithmetic logic unit (ALU) circuitry, floating point unit (FPU) circuitry, and a combinatorial logic block, for example, which can be used to execute instructions by performing logical operations such as AND, OR, NOT, NAND, NOR, and XOR, and invert (e.g., NOT) logical operations on data (e.g., one or more operands). For example, functional unit circuitry may be used to perform arithmetic operations such as addition, subtraction, multiplication, and division on operands via a number of operations.

DETAILED DESCRIPTION

Figure 1:
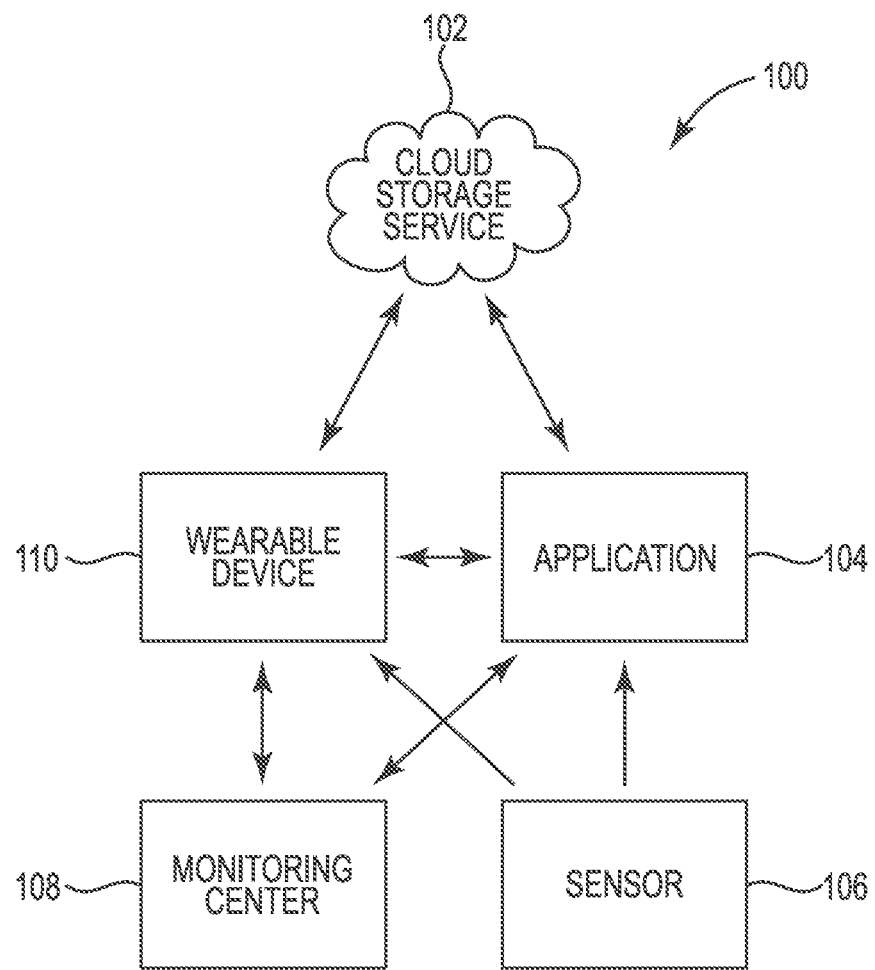
FIG. 1 is a diagram representing an example system for emergency assistance response in accordance with a number of embodiments of the present disclosure.

Apparatuses, machine-readable media, and methods related to monitoring health data and associated emergency assistance responses are described. Health related events can occur at any time. For instance, falls, blood glucose level spikes, blood pressure issues, etc. may occur when someone is alone or unable to get to a telephone. Some alert systems allow for a user to push a button and reach emergency services if the user needs help. However, such systems may not allow for automatic alerts (e.g., with little or no user interaction), tracking of health events, or communication with other health monitoring sensors, such as blood glucose monitors, heartrate monitors, or blood pressure monitors, among others.

Examples of the present disclosure can utilize a wearable device that is in communication with a control center, an application (e.g., an application downloaded on a mobile device or other computing device), a health data sensor, other devices (e.g., mobile devices of emergency contacts), a cloud storage service, or any combination thereof to work together as an emergency assistance response system to appropriately respond to an emergency or potential emergency. For instance, a wearer of the wearable device may experience an emergency, and the emergency assistance response system can determine an appropriate response.

Examples of the present disclosure can include a system comprising a non-transitory machine-readable medium comprising a first processing resource in communication with a memory resource having instructions executable to receive, at the first processing resource, first signaling from a second processing resource configured to monitor health data and track, at the first processing resource, the received first signaling. The instructions can be executable to identify, at the first processing resource or a different, third processing resource, output data representative of abnormal health data based on the tracked received first signaling and transmit the output data to a fourth processing resource of a wearable device.

The system can include the wearable device comprising the fourth processing resource to receive, at the fourth processing resource, the output data representative of the abnormal health data, provide a prompt via a user interface to a wearer of the wearable device associated with the abnormal health data, determine a response to the abnormal health data based on a reply or non-reply from the wearer via the user interface, and transmit the response to the first processing resource.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context.

The figures herein follow a numbering convention in which the first digit or digits correspond to the figure number and the remaining digits identify an element or component in the figure. Similar elements or components between different figures can be identified by the use of similar digits. For example, 110 can reference element "10" in FIG. 1, and a similar element can be referenced as 310 in FIG. 3. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a diagram representing an example system 100 for emergency assistance response in accordance with a number of embodiments of the present disclosure. The system 100 can include a cloud storage service 102, an application 104, such as an application downloaded on a mobile device or associated with a website, a sensor 106, a monitoring center 108, and a wearable device 110. While one sensor 106 is illustrated in FIG. 1, more or fewer sensors may be a part of the system 100.

The cloud storage service 102 can include cloud storage that allows a user (e.g., a wearer of the wearable device) to save data securely online so that it can be accessed anytime from any location and shared with those who are granted permission. The cloud storage service 102 may also allow a user to back up data to facilitate recovery off-site. The cloud storage service 102 can be in communication with the wearable device 110 and the application 104, which can also be in communication with one another.

The wearable device 110 can include, but is not limited to, a watch, a necklace, a ring, a wearable monitor, pendant, waterproof device, or other device that may be wearable. The wearable device 110 can include a processing resource in communication with a memory device to execute instructions. For instance, a wearer may fall and push a button on the wearable device 110 to call for help. The processing resource of the wearable device 110 can receive this request, write it the memory resource and communicate the request the application 104 and/or the monitoring center 108. The wearable device 110 can also transmit data to the cloud storage service 102 for storage and/or later retrieval. The wearable device 110 can also receive data from the sensor 106, which will be discussed further herein. In some examples, the wearable device 110 can include geolocation services (e.g., global positioning services (GPS)), such that the wearable device 110 can be located by a third party (e.g., for deployment of emergency services).

The application 104 may be a mobile application, website application, or desktop application and may include a computer program or software application designed to run on a mobile device or other computing device. The application 104 can receive data from the sensor 106, as will be discussed further herein, as well as sharing data with the wearable device 110, the monitoring center 108, and the cloud storage service 102. In some examples, the application 104 can be accessed via a user device, and data may be manually input. For instance, a user may input a desired ambulance service, insurance information, allergies, etc., such that the data is available to the monitoring center to aid in decision making for an emergency assistance response decision for or with the user.

The monitoring center 108 can be a staffed monitoring center (e.g., staffed 24 hours per day, 7 days per week) to receive communications from the wearable device 110 and/or the application 104. For instance, a user who falls while wearing the wearable device 110 may press a button that calls the monitoring center 108, or the application 104 may receive an indication from the wearable device 110 that the user has fallen and notify the monitoring center 108. In some examples, the monitoring center 108 can include a non-transitory machine-readable medium comprising a processing resource in communication with a memory resource having instructions executable to receive communication from the wearable device 110, the application 104, or both. Decisions at the monitoring center 108 may be made by trained responders, at the non-transitory machine-readable medium, or a combination thereof.

The sensor 106 can include a sensor to monitor health data. Examples may include, but are not limited to, heartrate monitors, blood pressure monitors, glucose monitors, oxygen level monitors, kidney function monitors, respiratory monitors, insulin pumps, or temperature sensors, among others. The sensor 106 can communicate collected data to the application 104, the wearable device 110, or both. For instance, if the sensor 106 detects an abnormal heartrate, an alert may be sent to the wearable device 110 to alert the wearer, and the data may also be sent to the application 104 for tracking. In some examples, the data can be transmitted from the wearable device 110 or the application 104 to the cloud storage service 102 for further storage. In some examples, the wearable device 110 can include a sensor on the wearable device (e.g., a built-in heartrate monitor, a temperature sensor, etc.).

Figure 2A:
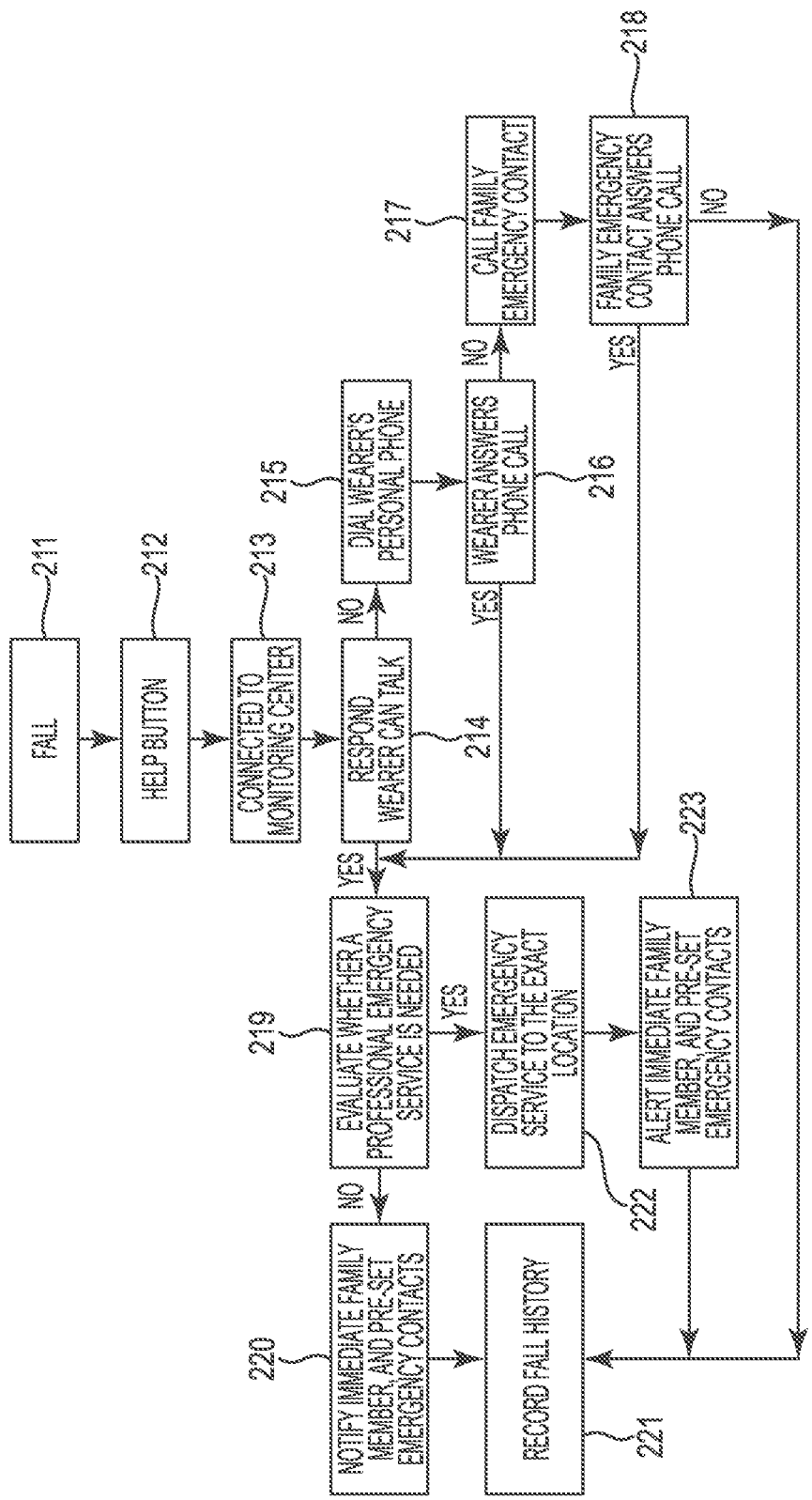
FIGS. 2A-2C are flow diagrams representing example methods for emergency assistance response in accordance with a number of embodiments of the present disclosure.
Figure 2B:
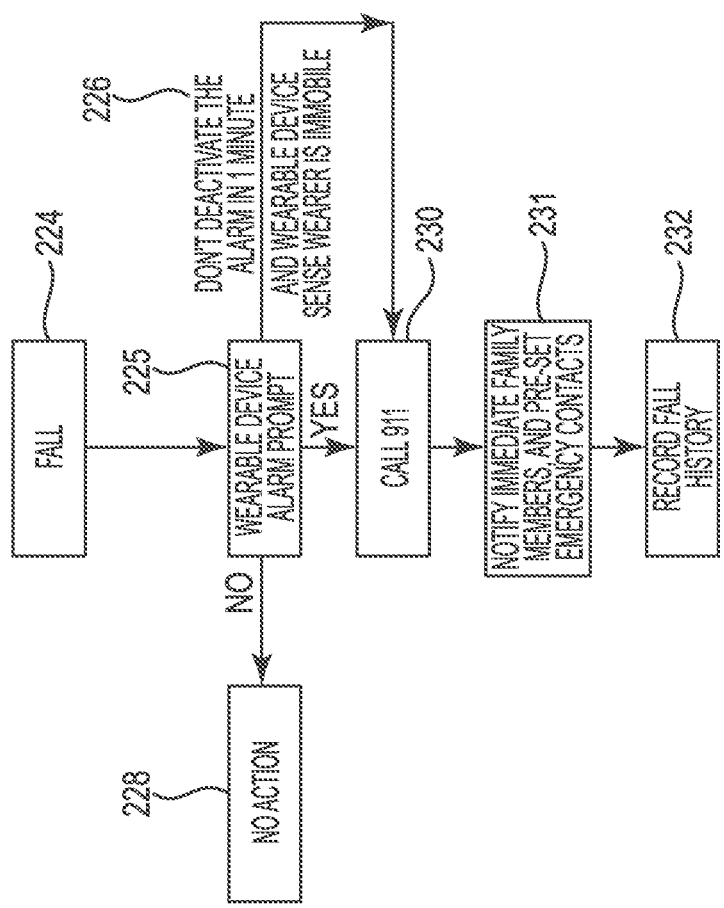
Figure 2C:
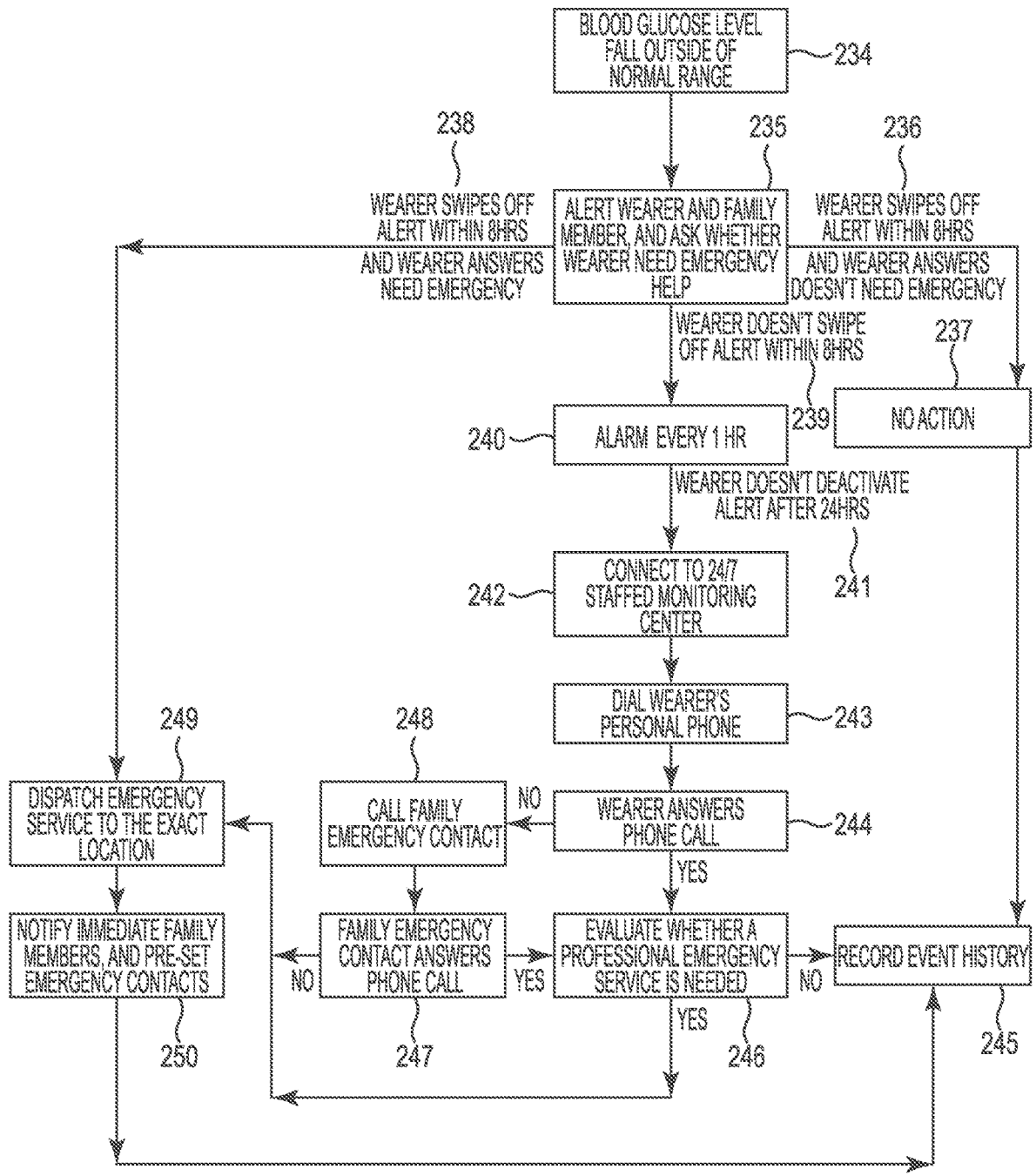

FIGS. 2A-2C are flow diagrams representing example methods for emergency assistance response in accordance with a number of embodiments of the present disclosure. FIG. 2A illustrates an example method flow in which a wearer of a wearable device, such as the wearable device 110 described with respect to FIG. 1 falls and presses a button on the wearable device to connect to a monitoring center, such as the monitoring center 108 described with respect to FIG. 1.

At 211, the wearer falls, and at 212, the wearer activates an emergency assistance response. This can include pushing a button, tapping something on a user interface of the wearable device, or some other triggering of a particular input on the wearable device. At 213, the wearer is connected to the monitoring center.

A responder at the monitoring center may speak or send a message to the wearer via the wearable device requesting a response. The responder may be a human responder, a program such as a trained machine learning model (e.g., artificial intelligence (AI)), or a combination thereof. If, at 214, the wearer is able to respond to the responder, for instance via voice or messaging via the wearable device, the responder can evaluate at 219 whether a professional emergency service is needed. For instance, if the responder determines the wearer has broken his or her leg, an evaluation may indicate an ambulance is necessary.

If, at 219, it is determined professional emergency services are needed, such emergency services can be dispatched at 222. For instance, the responder can send an ambulance to the location of the wearer using the geolocation services of the wearable device or based on information provided by the wearer. In addition, at 223, a family member and/or emergency contact can be contacted and provided with appropriate information. For instance, family members and/or emergency contacts, along with their contact information, can be entered into the application and made available to responders when an emergency assistance request is made. At 221, the fall can be tracked, recorded, and saved at the application and/or the cloud storage service for future reference.

If, at 219, it is determined emergency services are not needed, a family member and/or emergency contact may still be contacted at 220. For instance, if it is determined that the wearer has fallen and twisted his or her ankle, but is otherwise okay, the responder can contact one or more predetermined emergency contacts (e.g., pre-loaded into the application) and make him or her aware of the situation. Again, at 221, the fall can be tracked, recorded, and saved at the application and/or the cloud storage service for future reference.

If, at 214, it is determined that the wearer cannot respond, the responder can attempt, at 215, to call or communicate with the wearer via his or her personal phone or other device (e.g., mobile phone, landline, tablet with messaging, etc.). If, at 216, the wearer responds (e.g., answers a phone call), the method returns to 219 for an evaluation of the situation. If, at 216, the wearer does not respond, emergency contacts can be notified at 217. If, at 218, the emergency contacts are reached, the method returns to 219 for evaluation. If, at 218, the emergency contacts are not reachable, the fall history is recorded at 221. In such instances, emergency services may be dispatched to the location of the wearer, for instance, at 222.

FIG. 2B illustrates an example method flow in which a wearer of a wearable device, such as the wearable device 110 described with respect to FIG. 1, falls and an automatic emergency assistance response commences. At 224, the wearer falls, and at 225 the wearable device provides an alarm, prompt, or other notification to the wearer. For instance, the alarm, prompt, or other notification may include an audible alarm or notification, a vibration, a notification or prompt via a user interface of the wearable device, or a voice call via the wearable device or an associated mobile device. The alarm, prompt, or other notification can request confirmation from the wearer regarding whether he or she needs emergency assistance.

At 228, no action is taken if the wearer provides confirmation that he or she does not need emergency assistance. For instance, no emergency services are deployed, no emergency contacts are notified, and the alarm, prompt, or other notification is disabled. At 230, the wearable device automatically (e.g., with little or no user interaction) contacts emergency services (e.g., calls 911) if the wearer positively confirms in response to the alarm, prompt, or other notification that he or she needs emergency services.

If, at 226, the wearer does not deactivate the alarm, prompt, or other notification and/or the wearable device detects or senses the wearer is immobile (e.g., via sensors in/on or in communication with the wearable device), the method also proceeds to 230, where emergency services are automatically contacted (e.g., via the wearable device or the application). For instance, if the wearer does not deactivate the alarm, prompt, or other notification within a threshold time period (e.g., one minute), and a sensor of the wearable device determines the wearable device is immobile emergency services are automatically contacted at 230 (e.g., "911" is called). In some examples, the alarm, prompt, or other notification may be deactivated within the threshold time period, and the wearer may indicate he or she does not need help. In such an example, no action is taken at 228. In some instances, the alarm, prompt, or other notification may be deactivated within the threshold time period, but the user may indicate he or she does need help. In such an example, emergency services can be contacted at 230.

At 231, family members and emergency contacts are notified, and at 232, the fall history is recorded, for instance at a cloud storage service. While a fall is described with respect to FIGS. 2A and 2B, other incidents may result in a user triggering an input of the wearable device or an automatic response.

FIG. 2C illustrates an example in which a wearer of a wearable device, such as the wearable device 110 described with respect to FIG. 1 suffers an abnormal health event detected by a sensor such as the sensor 106 described with respect to FIG. 1. The example illustrated in FIG. 2C includes the use of a single sensor, in this example a glucose monitor, but more than one sensor may be present, and different types of sensors may be present (e.g., heartrate monitor, oxygen level monitor, etc.).

At 234, a sensor detects that an abnormal health event has occurred, in this example, a blood glucose level falling outside of a normal, threshold range. At 235, a wearer of a wearable device is alerted. In addition, a family member or emergency contact may also be notified. For instance, family members or emergency contacts may be added, along with their contact information, via an application in communication with the wearable device. At 235, the wearer and the family member or emergency contact can be prompted for a response regarding whether or not he or she needs emergency assistance.

If, at 236, the wearer dismisses the alert within a threshold time period, for instance he or she swipes away a notification within eight hours, no action is taken at 237. At 236, the wearer's dismissal may act as the confirmation that no help is requested, or a separate confirmation can be received at the wearable device that the wearer does not need emergency assistance. At 245, the abnormal health data (e.g., high glucose level) is recorded and stored, for instance at a cloud storage service in communication with the wearable device and/or application.

If, at 238, the wearer dismisses the alert within the threshold time, but also indicates that emergency assistance is needed, emergency services can be dispatched at 249. For instance, a responder at a monitoring center, whether a person, a machine learning model, or a combination thereof, can dispatch emergency services to a location of the wearable device based on communication from the wearer and/or geolocation services on the wearable device. At 250, the family or emergency contacts can be notified, and at 245, the abnormal health data and response can be tracked and stored, for instance with a cloud storage service.

At 239, if the wearable device does not receive input from the wearer in response to the alert provided at 235 (e.g., the wearer does not dismiss the alert), an alarm or other notification can be transmitted, at 240, to the wearable device at regular intervals, for instance, every hour for a threshold amount of time. If the wearer responds to one of those reminder alerts, the method proceeds to either 236 or 238, as appropriate. However, if at 241, the wearer does not dismiss or deactivate the alert after the threshold time period (e.g., 24 hours), the wearer can be connected to the monitoring center at 242. For instance, a staffed or unstaffed (e.g., using machine learning models) monitoring center can be alerted, and at 243, a user device associated with the wearable device can be contacted at 243. For instance, a personal phone number provided previously via the application can be called or a text message can be sent.

If, at 244, the wearer answers his or her phone, responds to a text, etc., a responder at the monitoring center can evaluate whether a professional emergency service is needed at 246. For instance, based on the abnormal health data, event history tracked and stored in the cloud storage service, and a conversation with the wearer, it may be determined that no emergency assistance is necessary. In such an example, the abnormal health data and response is tracked and stored at 245. If, however, at 246, it is determined that emergency assistance is needed, emergency services can be dispatched to the wearer's location at 249, a family member or emergency contact can be notified at 250, and the abnormal health data and response can be tracked and stored at 245.

If, at 244, the wearer does not answer his or her phone, responds to a text, etc., a responder at the monitoring center can contact the family member or emergency contact at 248. If, at 247, the family member or emergency contact is reached, the method can proceed to evaluation of whether professional emergency services are needed at 246. If, at 247, the family member or emergency contact cannot be reached, the method can proceed to dispatch of emergency services to a location of the wearer (e.g., a location of the wearable device based on geolocation services) at 249.

Figure 3:
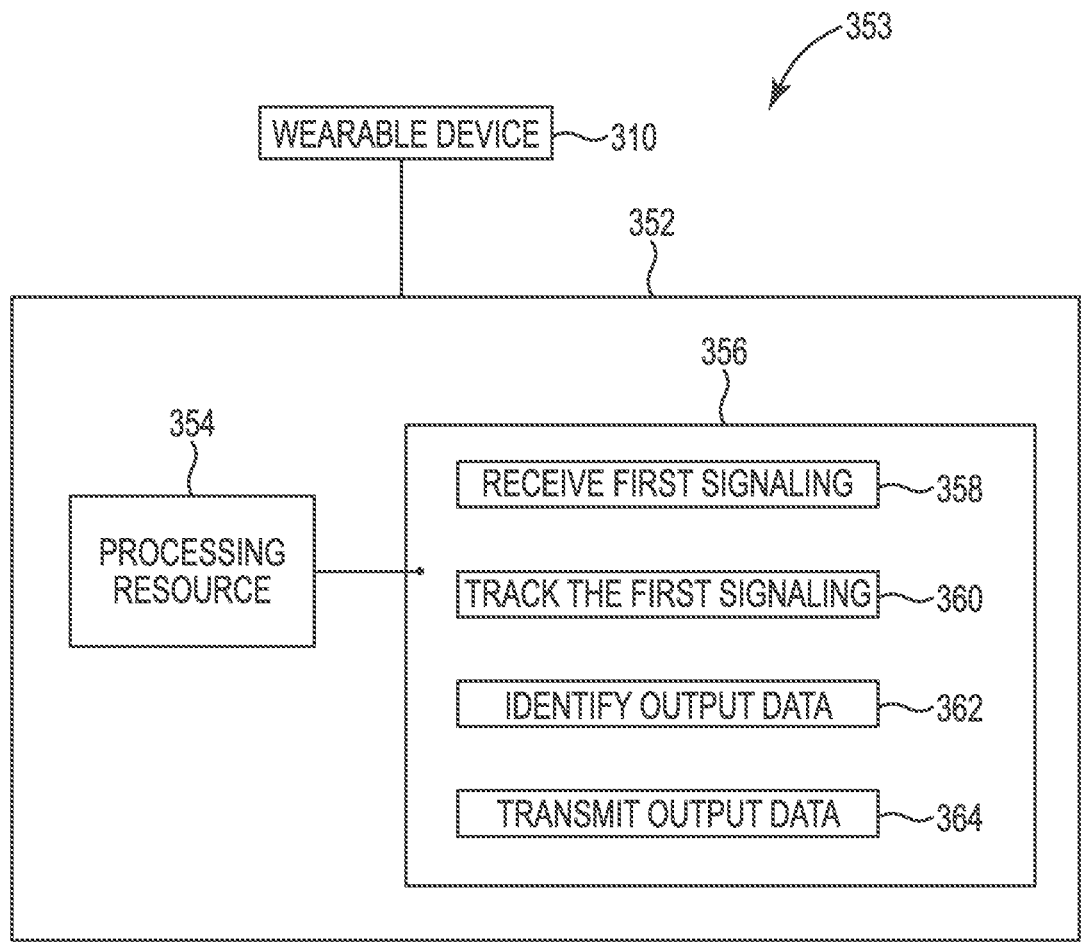
FIG. 3 is a functional diagram representing a wearable device and a processing resource in communication with a memory resource having instructions written thereon in accordance with a number of embodiments of the present disclosure.

FIG. 3 is a functional diagram representing a wearable device 310 and a processing resource 354 in communication with a memory resource 356 having instructions 358, 360, 362, 364 written thereon in accordance with a number of embodiments of the present disclosure. In some examples, the processing resource 354 and memory resource 356 comprise a first system 352, and together with wearable device 310, comprise a second system 353. The second system 353, in some examples, may include more or fewer elements including, for instance, a cloud storage service, a monitoring center, and/or a sensor. For example, the system 353 may be analogous or similar to the system 100 described with respect to FIG. 1.

The first system 352 illustrated in FIG. 3 can be a server or a computing device (among others) and can include the processing resource 354. The system 352 can further include the memory resource 356 (e.g., a non-transitory MRM), on which may be stored instructions, such as instructions 358, 360, 362, 364. Although the following descriptions refer to a processing resource and a memory resource, the descriptions may also apply to a system with multiple processing resources and multiple memory resources. In such examples, the instructions may be distributed (e.g., stored) across multiple memory resources and the instructions may be distributed (e.g., executed by) across multiple processing resources. In some examples, the first system 352 can comprise a mobile, website, or desktop application.

The memory resource 356 may be an electronic, magnetic, optical, or other physical storage device that stores executable instructions. Thus, the memory resource 356 may be, for example, non-volatile or volatile memory. For example, non-volatile memory can provide persistent data by retaining written data when not powered, and non-volatile memory types can include NAND flash memory, NOR flash memory, read only memory (ROM), Electrically Erasable Programmable ROM (EEPROM), Erasable Programmable ROM (EPROM), and Storage Class Memory (SCM) that can include resistance variable memory, such as phase change random access memory (PCRAM), three-dimensional cross-point memory, resistive random access memory (RRAM), ferroelectric random access memory (FeRAM), magnetoresistive random access memory (MRAM), and programmable conductive memory, among other types of memory. Volatile memory can require power to maintain its data and can include random-access memory (RAM), dynamic random-access memory (DRAM), and static random-access memory (SRAM), among others.

In some examples, the memory resource 356 is a non-transitory MRM comprising Random Access Memory (RAM), an Electrically-Erasable Programmable ROM (EEPROM), a storage drive, an optical disc, and the like. The memory resource 356 may be disposed within a controller and/or computing device. In this example, the executable instructions 358, 360, 362, 364 can be "installed" on the device. Additionally, and/or alternatively, the memory resource 356 can be a portable, external or remote storage medium, for example, that allows the system to download the instructions 358, 360, 362, 364 from the portable/external/remote storage medium. In this situation, the executable instructions may be part of an "installation package". As described herein, the memory resource 356 can be encoded with executable instructions for an emergency assistance response.

The instructions 358, when executed by a processing resource such as the processing resource 354 (herein after referred to as the "first processing resource 354"), can include instructions to receive at the first processing resource 354, first signaling from a second processing resource configured to monitor health data. For instance, the second processing resource can comprise a sensor communicatively coupled to the wearable device 310 and the non-transitory machine readable medium 356 to monitor the health data of a wearer of the wearable device 310. For instance, the sensor can include a heartrate monitor, glucose monitor, or other health data monitor that can transmit a notification to the wearable device 310 or an application 352 in communication with the sensor and the wearable device 310. For instance, the second processing resource of the sensor can transmit the first signaling to the first processing resource and a fourth processing resource of the wearable device 310.

The instructions 360, when executed by a processing resource such as the first processing resource 354, can include instructions to track, at the first processing resource 354, the received first signaling. For instance, if a wearer receives health data at the first processing resource 354, such received data can be tracked via the application and/or tracked and stored in a cloud computing service coupled to the application and wearable device. Tracking the health data may allow for pattern recognition of abnormal health data or events and may be useful to a responder when determining an emergency assistance response.

The instructions 361, when executed by a processing resource such as the first processing resource 354, can include instructions to identify, at the first processing resource or a different, third processing resource, output data representative of abnormal health data based on the tracked received first signaling. For instance, if the received health data indicates an elevated heartrate or abnormal (e.g., above threshold) glucose level, the output data can include an alert to transmit to the wearable device indicating emergency assistance may be needed.

For instance, the instructions 364, when executed by a processing resource such as the first processing resource 354, can include instructions to transmit the output data to a fourth processing resource of a wearable device. A prompt, alarm, or other alert can be transmitted to the wearable device for input from the wearer to determine whether emergency assistance is needed or requested based on the abnormal health data.

The wearable device 310 can receive, at the fourth processing resource, the output data representative of the abnormal health data. The output data may present itself as a badge on a wearable device, an audible alarm, a physical notification, etc. For instance, the wearable device 310 can provide a prompt via a user interface to a wearer of the wearable device 310 associated with the abnormal health data. For instance, the wearable device 310 may audibly ask the wearer if he or she needs emergency assistance, or a badge may be presented for the wearer to ignore, engage, or dismiss. In some examples, additional information may be requested from the user via the wearable device 310. For instance, the wearer may be prompted via the user interface.

A determination, for instance, via the fourth processing resource of the wearable device 354 or the application, can be made with respect to a response to the abnormal health data based on a reply or non-reply from the wearer via the user interface. For instance, it can be determined that the response is a request for help in response to the reply including confirmation of the request for help within a threshold period of time. For instance, a wearer may press a confirmation button or badge, or he or she may provide verbal confirmation that help is requested/needed.

In some instances, it can be determined that the response is not a request for help in response to the reply including confirmation, within the threshold period of time, that no action is requested. For example, a wearer may swipe away a badge displayed on a user interface of the wearable device 310 indicating her or she is not requesting help, or the wearer may reply by voice or text that emergency assistance is not requested or needed.

The response, in some instances, can be determined to be unknown in response to a non-reply. An unknown response may prompt follow-up alerts to the wearable device 310 or communication with family or emergency contacts of the wearer. For instance, the wearable device 310 can provide a follow-up prompt within a predetermined time period and via the user interface of the wearable device 310 in response to the non-reply. If the wearer responds at that time, an emergency assistance response can be determined based on the wearer's response. In some examples, the wearable device 310 can determine the response is a request for help if there is another non-reply after the follow-up prompt, or after a threshold time period or number of follow-up prompts. For instance, if after ten prompts, the wearer does not respond, emergency assistance can be sent to the location of the wearer (e.g., based on geolocation services on the wearable device 310) and/or family and emergency contacts can be notified. Such contacts may be entered, along with other information such as insurance, preferred hospitals and doctors, etc. via the application.

The wearable device 310 can transmit the response to the first processing resource 354. The first processing resource 354 may execute instructions for tasks or notifications. For instance, when contacting a family member or emergency contact, the first processing resource can transmit the response received from the wearable device 310 to a fifth processing resource associated with a user device of a family member or an emergency contact of the wearer. In some examples, the first processing resource 354 to transmit the response received from the wearable device 310 to a sixth processing resource associated with a monitoring center. For instance, a responder at a monitoring center can aid in an emergency assistance response decision using the health data, tracked and stored health data (e.g., stored with a cloud storage service), and input from the wearer, family, or emergency contacts.

Figure 4:
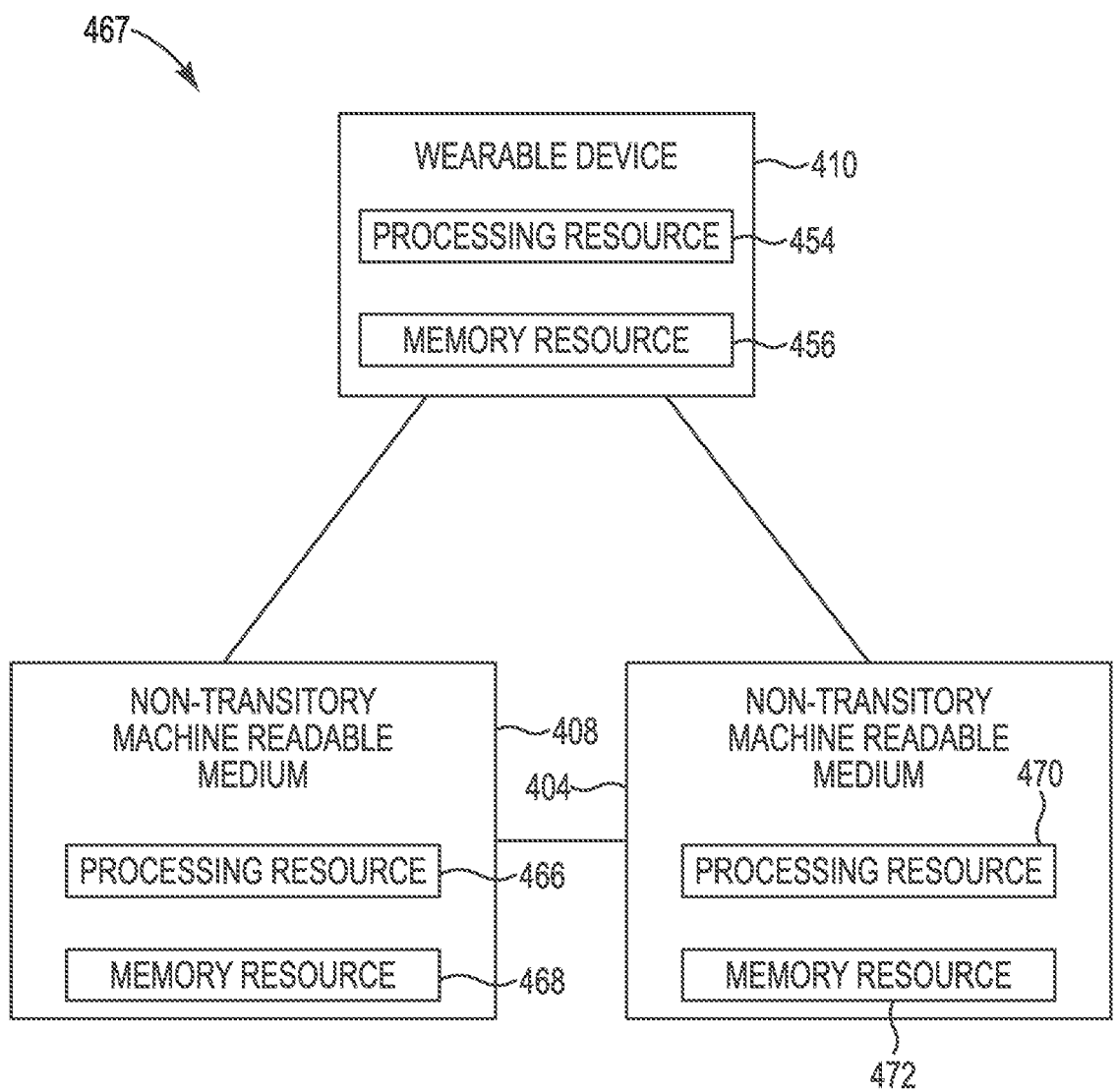
FIG. 4 is another diagram representing an example system for emergency assistance response including a wearable device and processing resources in communication with memory resources in accordance with a number of embodiments of the present disclosure.

FIG. 4 is another diagram representing an example system 467 for emergency assistance response including a wearable device 410 and processing resources 454, 466, 470 in communication with memory resources 456, 468, 472 in accordance with a number of embodiments of the present disclosure. The memory resources 456, 468, 472 can include instructions thereon that are executable by their respective processing resources 454, 466, 470 to perform actions with respect to an emergency assistance response. The system 467, in some examples, may be analogous to systems 100 and/or 353 described with respect to FIGS. 1 and 3.

The wearable device 410 can include the processing resource 454 (herein after referred to as the "first processing resource 454") in communication with the memory resource 456 (herein after referred to as the "first memory resource 456") or other storage. The wearable device 410 can receive, at the first processing resource 454, a request for emergency assistance. This request can include the first processing resource 454 receiving indication of triggering of a particular input on the wearable device 410. For instance, a wearer may push a button on the wearable device 410 indicating he or she needs help (e.g., emergency assistance).

In some examples, the request for emergency assistance comprises detection of, by the first processing resource 454 or a sensor in communication with the first processing resource 454, a health event. For instance, an oxygen level monitor may transmit a low oxygen level to the wearable device 410 and display the level, an alert, or another notification/query regarding emergency assistance needs. While a low oxygen level is used herein as an example health events, other health events are possible including indications of abnormal health data (e.g., high glucose level, high blood pressure, etc.). In some examples, the wearable device 410 may have a built-in sensor in communication with the first processing resource 454 to detect a health event (e.g., a fall sensor, immobility sensor, etc.).

The wearable device 410 can transmit the request to the second processing resource 466 in communication with the second memory resource 468 of the non-transitory machine-readable medium 408, for instance located at a monitoring center, which can receive the request and route the request to an emergency contact, an emergency service, or both.

The non-transitory machine-readable medium 404 that includes the third processing resource 470 in communication with the third memory resource 472 can track the request and an associated response. For instance, the third processing resource 470 may be associated with a mobile, website, or desktop application in communication with the wearable device and can collect and track health data and events. The application and/or the wearable device 410 may also transmit health data to a cloud storage service for tracking and/or storage. Tracking the data can be useful for future emergency assistance requests, for instance. In some instances, the wearable device 410 can transmit the request directly to the third processing resource 470 for tracking.

In some examples, the third processing resource 470 can receive second signaling from the third processing resource 470 configured to monitor health data. For instance, a sensor such as the aforementioned oxygen level monitor, may transmit an indication of abnormal health data to the third processing resource 470 for tracking.

In some examples, the non-transitory machine readable medium 408, the second non-transitory machine readable medium 404, or both, can include instructions executable to transmit an alert, a request for response, or both, to the wearable device 410 in response to the request for emergency assistance. For instance, a wearer may fall and push a button on the wearable device 410 indicating he or she needs help (e.g., emergency assistance). In response an alert, a request for response, or both can be sent to the wearable device 410. An alert, for instance, can include an audible alarm, badge display, or message, among others. A request for response can include, for instance, a badge that must be displayed to clear the request or a prompt to confirm that emergency assistance is indeed requested. If such confirmation is received, emergency assistance may be deployed or a responder at a monitoring center in communication with the wearable device 410 may further communicate with the wearer.

Figure 5:
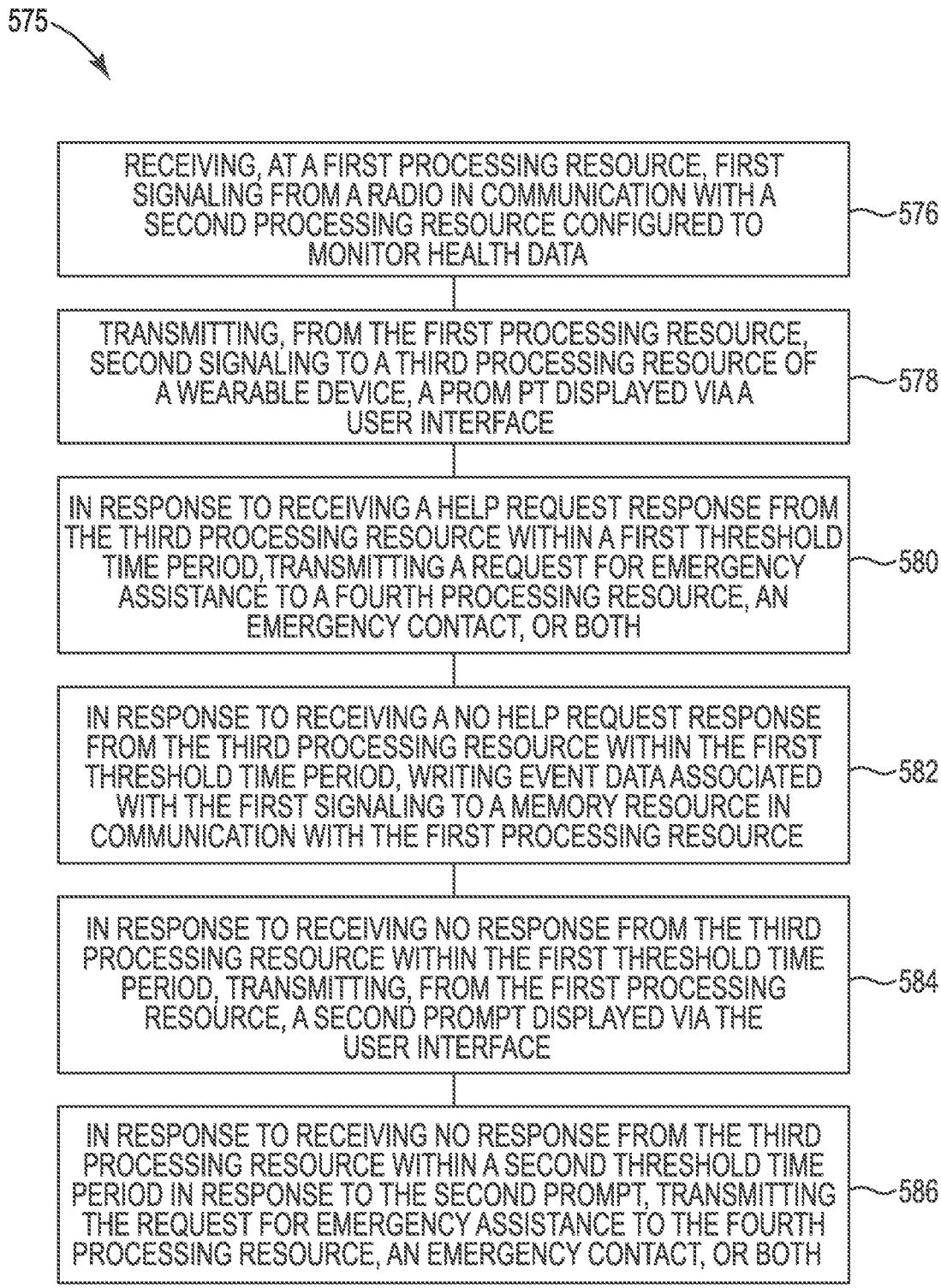
FIG. 5 is another flow diagram representing an example method for emergency assistance response in accordance with a number of embodiments of the present disclosure.

FIG. 5 is another flow diagram representing an example method 575 for emergency assistance response in accordance with a number of embodiments of the present disclosure. The method 575 can be performed by a system such as the systems described with respect to FIGS. 1, 3, and 4.

At 576, the method 575 can include receiving, at a first processing resource, first signaling from a second processing resource configured to monitor health data. For instance, the first processing resource can receive data from a sensor that is monitoring health data of a wearer, such as a heartrate, blood pressure, blood glucose levels, insulin pump levels, kidney functions, or other monitored health functions. In some examples, more than one sensor may be in communication with the first processing resource.

In some examples, the first signaling, for instance, can be representative of abnormal health data. For instance, a user may be experiencing higher-than-normal (e.g., above a threshold) blood pressure. In one example, the first signaling is received at an application that a wearer of a wearable device has customized with applicable personal health data thresholds (e.g., threshold blood pressure, blood glucose levels, etc.), as well as other individual information such as family contacts, emergency contacts, insurance information, allergies, physician contact information, preferred healthcare providers, etc. In some examples, the wearable device may receive the first signaling, as well.

At 578, the method 575 can include transmitting, from the first processing resource, second signaling to a third processing resource of a wearable device, a prompt displayed via a user interface. For instance, if the first signaling is abnormal health data, that information can be transmitted to the wearable device for the wearer to see and evaluate. In some examples, transmitting the second signaling can include triggering an audible alarm, visual alarm, physical alarm, or any combination thereof via the wearable device. For instance, if the wearer's blood pressure is higher than a threshold, an alarm may sound, and the user may determine emergency assistance is needed. He or she may trigger an input on the wearable device to request assistance.

The method 575, at 580, can include transmitting a request for emergency assistance to a fourth processing resource, an emergency contact, or both, in response to receiving a help request response from the third processing resource within a first threshold time period. For instance, an application may receive the help request via the wearable device and transmit the request to a monitoring center, family member, or emergency contact. In some examples, the wearable device may be in communication with the monitoring center, and the monitoring center may receive the request simultaneously with the application. For instance, the fourth processing resource can be part of a monitoring center that provides additional assessments when determining an emergency assistance response.

At 582, the method 575 can include writing event data associated with the first signaling to a memory resource in communication with the first processing resource in response to receiving a no help request response from the third processing resource within the first threshold time period. For instance, if the wearer confirms he or she does not need help by dismissing the alert or communicating with a monitoring center that no help is needed, the request is dismissed, tracked, and stored. In some instances, the tracking and/or storing occurs with cloud storage service.

At 584, the method 575 can include transmitting, from the first processing resource, a second prompt displayed via the user interface in response to receiving no response from the third processing resource within the first threshold time period. For example, if the wearer does not respond to the prompt, he or she will be notified again regarding the abnormal health data. If he or she responds that no help is needed, the request is dismissed, tracked, and stored.

The method 575, at 586, can include transmitting the request for emergency assistance to the fourth processing resource, an emergency contact, or both in response to receiving no response from the third processing resource within a second threshold time period in response to the second prompt. For instance, if the wearer does not respond to the second prompt, emergency assistance may be deployed to the location of the wearer, which may be determined using geolocation services on the wearable device. The abnormal health data and associated response can be tracked and stored. For instance, regardless of the response, the method 575 can include tracking at the first processing resource and storing at the memory resource or other storage (e.g., a cloud storage service), the first signaling and the help request, no help request, or non-response, as well as any associated response (e.g., deployed emergency assistance, contacted family, etc.).

In some examples, the method 575 can include receiving, at the first processing resource, third signaling from a fifth processing resource configured to monitor different health data, and transmitting, from the first processing resource, fourth signaling to the third processing resource of the wearable device, a different prompt associated with the different health data and displayed via the user interface. In such examples, more than one sensor may monitor health data for a wearer. For instance, a user may have a blood glucose monitor and an insulin pump providing health data to the wearable device and/or associated application. The wearer can be prompted via the wearable device and/or or the application of abnormal health data from each of the different sensors. Health data from both sensors may be tracked and stored to aid future emergency assistance response decisions.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system, comprising:
a non-transitory machine-readable medium comprising a first processor in communication with a memory resource having instructions executable to:
  receive, at the first processor, first signaling from a second processor configured to monitor health data;
  track, at the first processor, the received first signaling;
  identify, at the first processor or a different, third processor, output data representative of abnormal health data based on the tracked received first signaling; and
  transmit the output data to a fourth processor of a wearable device; and
a wearable device comprising the fourth processor to:
  receive, at the fourth processor, the output data representative of the abnormal health data;
  provide a prompt via a user interface to a wearer of the wearable device associated with the abnormal health data;
  determine a response to the abnormal health data based on a reply or non-reply from the wearer via the user interface;
  transmit the response to the first processor;
  determine the response is a request for help in response to the reply including confirmation, within a threshold period of time, of the request for help;
  determine the response is not a request for help in response to the reply including confirmation, within the threshold period of time, that no action is requested;
  determine the response is unknown in response to the non-reply;
  provide a follow-up prompt within a predetermined time period and via the user interface in response to the non-reply; and
  determine the response is a request for help in response to another non-reply from the wearer via the user interface after the follow-up prompt.

2. The system of claim 1, wherein the second processor configured to monitor health data comprises a sensor communicatively coupled to the wearable device and the non-transitory machine-readable medium to:
  monitor the health data of a wearer of the wearable device; and
  transmit the first signaling to the first processor and the fourth processor.

3. The system of claim 1, further comprising the first processor to transmit the response received from the wearable device to a fifth processor associated with a user device of an emergency contact of the wearer.

4. The system of claim 1, further comprising the first processor to transmit the response received from the wearable device to a sixth processor associated with a monitoring center.

5. The system of claim 4, further comprising:
the wearable device to:
  determine the response is a request for help in response to the reply including confirmation, within a threshold period of time, of the request for help; and
  transmit the response to the first processor, the sixth processor, or both; and
  in response, the sixth processor to dispatch emergency services to a tracked location of the wearable device.

6. A method, comprising:
receiving, at a first processor, first signaling from a second processor configured to monitor health data;
transmitting, from the first processor, second signaling to a third processor of a wearable device, a prompt displayed via a user interface;
in response to receiving a help request response from the third processor within a first threshold time period, transmitting a request for emergency assistance to a fourth processor, an emergency contact, or both;
in response to receiving a no help request response from the third processor within the first threshold time period, writing event data associated with the first signaling to a memory resource in communication with the first processor;
in response to receiving no response from the third processing processor within the first threshold time period, transmitting, from the first processor, a second prompt displayed via the user interface; and
in response to receiving no response from the third processor within a second threshold time period in response to the second prompt, transmitting the request for emergency assistance to the fourth processor, an emergency contact, or both.

7. The method of claim 6, wherein transmitting the request for emergency assistance to the fourth processor comprises transmitting the request to a monitoring center for additional assessment.

8. The method of claim 6, further comprising tracking at the first processor and storing at the memory resource the first signaling and the help request, no help request, or non-response.

9. The method of claim 6, wherein receiving the first signaling at the first processor comprises receiving first signaling representative of abnormal health data.

10. The method of claim 6, further comprising:
receiving, at the first processor, third signaling from a fifth processor configured to monitor different health data; and
transmitting, from the first processor, fourth signaling to the third processor of the wearable device, a different prompt associated with the different health data and displayed via the user interface.

11. The method of claim 6, wherein:
receiving the first signaling at the first processor comprises receiving first signaling representative of abnormal health data; and
transmitting the second signaling to the third processor of the wearable device comprises triggering an audible alarm, visual alarm, physical alarm, or any combination thereof via the wearable device.

12. A system, comprising:
a wearable device comprising a first processor to:
receive a request for emergency assistance;
write the request to a first memory resource in communication with the first processor;
provide a prompt via a user interface to a wearer of the wearable device;
determine a response to the emergency assistance based on a reply or non-reply from the wearer via the user interface;
confirm the response is a request for help in response to the reply including confirmation, within a threshold period of time, of the request for emergency assistance;
determine the response is not a request for help in response to the reply including confirmation, within the threshold period of time, that no emergency assistance is requested;
determine the response is unknown in response to the non-reply;
provide a follow-up prompt within a predetermined time period and via the user interface in response to the non-reply; and
confirm the response is a request for help in response to another non-reply from the wearer via the user interface after the follow-up prompt; and
transmit the request to a second processor via first signaling from the second processor;
a first non-transitory machine-readable medium in communication with the first processor and comprising the second processor in communication with a second memory resource having instructions executable to:
receive the request; and
route the request to an emergency contact, an emergency service, or both; and
a second non-transitory machine-readable medium in communication with the first processor and the second processor and comprising a third processor in communication with a third memory resource having instructions executable to track the request and an associated response.

13. The system of claim 12, wherein the request for emergency assistance comprises the first processor receiving indication of triggering of a particular input on the wearable device.

14. The system of claim 12, wherein the request for emergency assistance comprises detection of, by the first processor or a sensor in communication with the first processor, a health event.

15. The system of claim 12, further comprising the first processor to transmit the request to the third processor.

16. The system of claim 12, further comprising the third processing first processor to receive second signaling from the third processor configured to monitor health data.

17. The system of claim 12, further comprising the first non-transitory machine readable medium, the second non-transitory machine readable medium, or both, comprising instructions executable to transmit an alert, a request for response, or both, to the wearable device in response to the request for emergency assistance.

* * * * *